US012582383B2

(12) United States Patent
Kim et al.

(10) Patent No.: US 12,582,383 B2
(45) Date of Patent: Mar. 24, 2026

(54) ULTRASOUND IMAGE PROCESSING METHOD, AND ULTRASOUND APPARATUS USING THE SAME

(71) Applicant: SAMSUNG MEDISON CO., LTD., Gangwon-do (KR)

(72) Inventors: Kang Sik Kim, Hongcheon-Gun (KR); Yang Mo Yoo, Seoul (KR); Young Ray Kim, Seoul (KR); Jung Ho Kim, Hongcheon-Gun (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 102 days.

(21) Appl. No.: 18/139,718

(22) Filed: Apr. 26, 2023

(65) Prior Publication Data

US 2023/0371927 A1 Nov. 23, 2023

(30) Foreign Application Priority Data

May 20, 2022 (KR) ........................ 10-2022-0062344
Nov. 17, 2022 (KR) ........................ 10-2022-0154810

(51) Int. Cl.
*A61B 8/00* (2006.01)

(52) U.S. Cl.
CPC .......... *A61B 8/4483* (2013.01); *A61B 8/4427* (2013.01); *A61B 8/5215* (2013.01)

(58) Field of Classification Search
CPC ... A61B 8/4483; A61B 8/4427; A61B 8/5215; G01S 15/8927; G01S 15/8997; G01S 7/52047
See application file for complete search history.

(56) References Cited

U.S. PATENT DOCUMENTS 6,231,511 B1 5/2001 Bae
8,241,216 B2 8/2012 Loftman et al.
(Continued)

FOREIGN PATENT DOCUMENTS

EP 3207878 A1 8/2017
JP 2004-201864 A 7/2004
(Continued)

OTHER PUBLICATIONS

Nikolov et al., "Parameter study of 3D synthetic aperture post-beamforming procedure", 2006, Ultrasonics, vol. 44, p. e159-e164, XP025009161.

(Continued)

*Primary Examiner* — Peter Luong
(74) *Attorney, Agent, or Firm* — Morgan Lewis & Bockius LLP

(57) ABSTRACT

An ultrasound image processing method according to an embodiment of the present disclosure includes transmitting and receiving an ultrasound signal to and from an object through an array in which a plurality of apertures are arranged along one direction, calculating at least one of a transmission delay and a reception delay of the ultrasound signal, and forming a multi-beam through synthetic focusing by reflecting the calculated delay on the ultrasound signal received by the array, wherein the calculating of the delay is calculated through a propagation shape model in which the ultrasound signal transmitted or received through the array is centered on virtual sources parallel to the array.

13 Claims, 15 Drawing Sheets

(56) References Cited

U.S. PATENT DOCUMENTS

| | | | |
|---|---|---|---|
| 9,366,753 | B2 | 6/2016 | Hoctor et al. |
| 10,993,701 | B2 | 5/2021 | Ikeda et al. |
| 11,160,533 | B2 | 11/2021 | Takano |
| 2009/0069692 | A1* | 3/2009 | Cooley .............. G01S 7/52095 |
| | | | 600/459 |
| 2016/0174938 | A1 | 6/2016 | Takano |

FOREIGN PATENT DOCUMENTS

| | | | |
|---|---|---|---|
| JP | 5949090 | B2 | 7/2016 |
| JP | 5967901 | B2 | 7/2016 |
| JP | 644518 | B2 | 12/2018 |
| KR | 10-0280197 | B1 | 2/2001 |
| WO | 2013/069752 | A1 | 5/2013 |

OTHER PUBLICATIONS

Extended European Search Report issued Oct. 10, 2023 for counterpart European Patent Application No. 23164689.4.

* cited by examiner

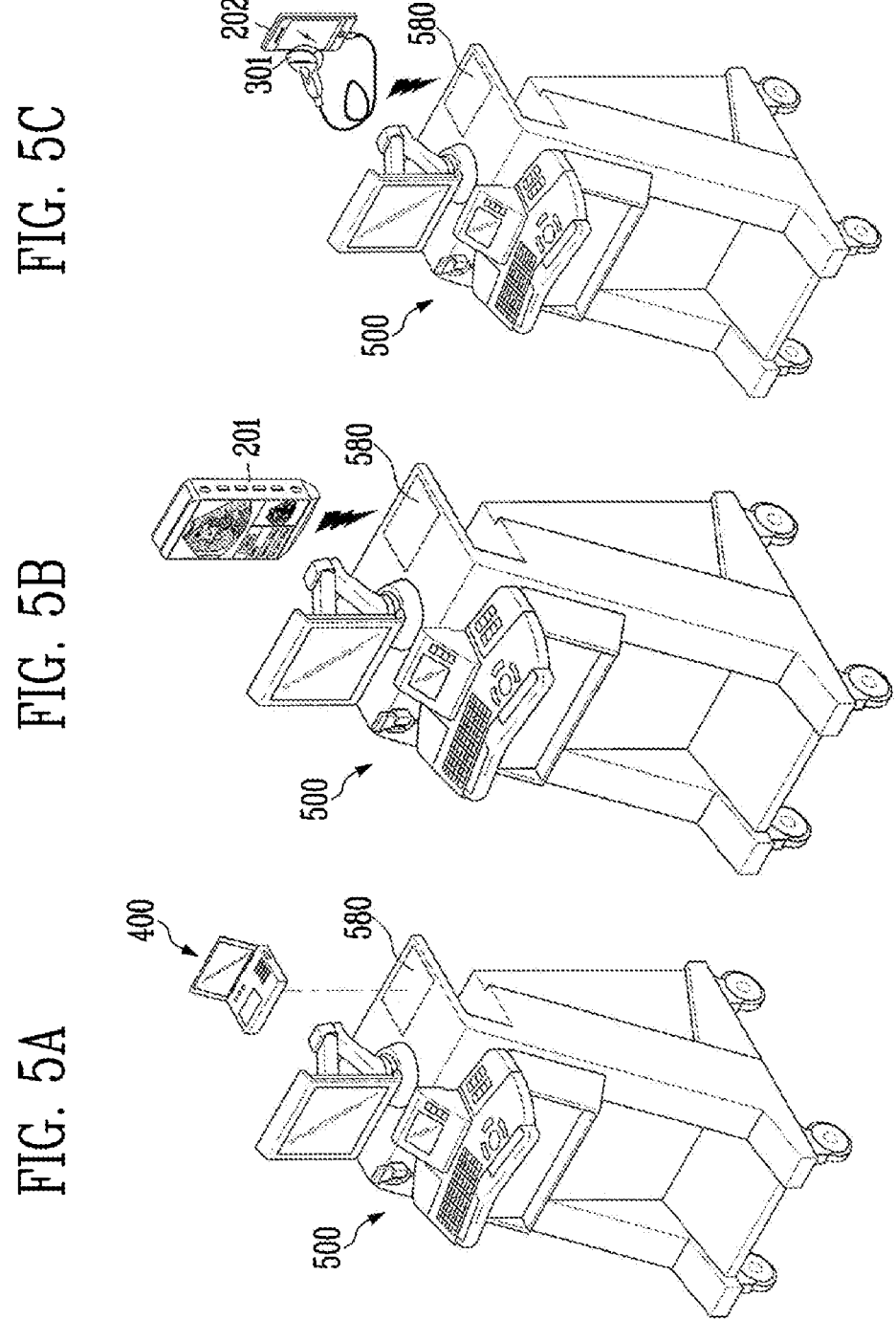

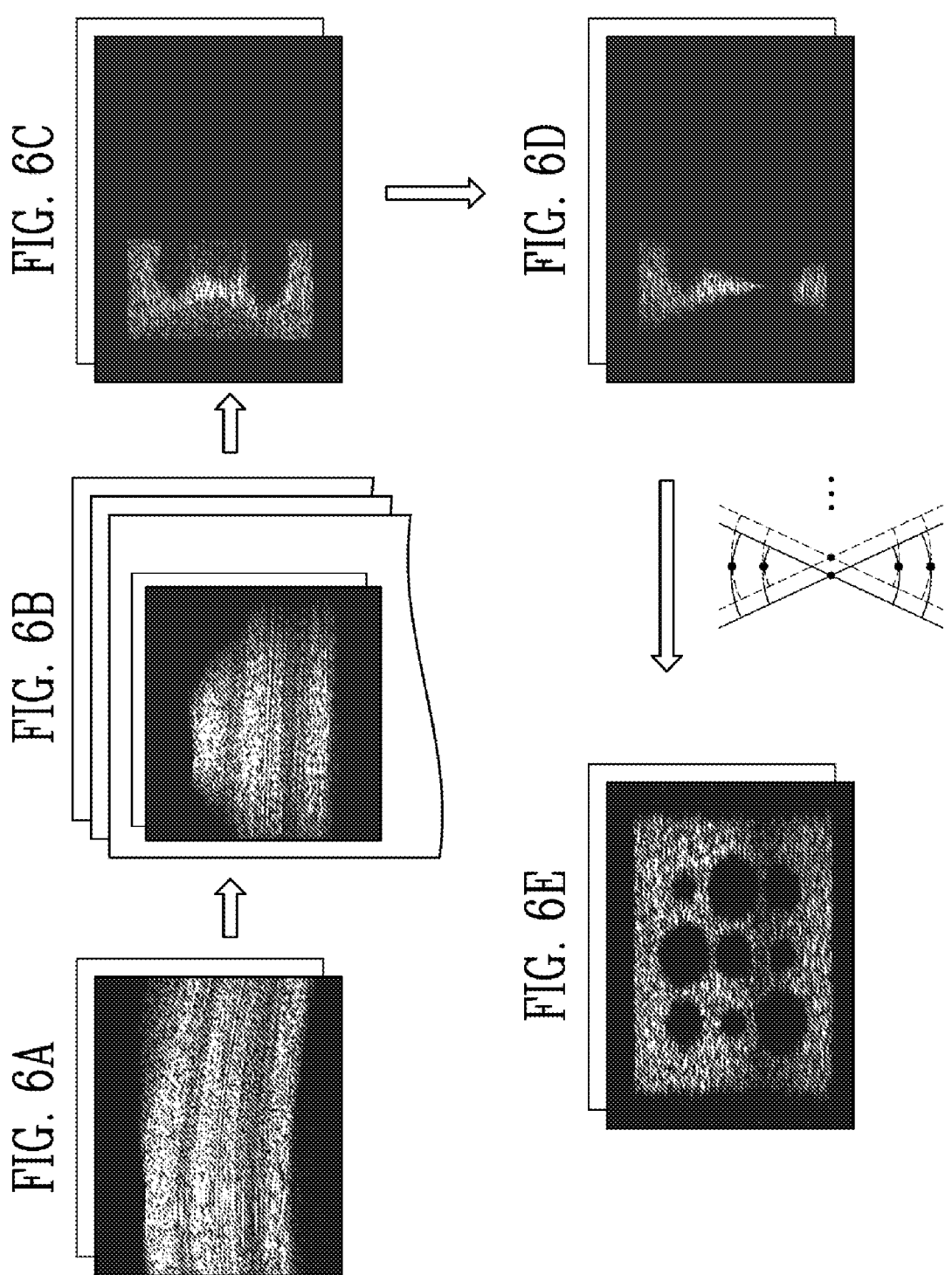

Beam Source

Image Source $(x_s, z_s)$

Element $(x_e, z_e)$

Aperture $d_f$

Dynamic RX focusing

Image Point $(x_i, z_i)$ $d_{c1}$ $d_{c2}$

Ellipse Focus $(x_f - x_c, z_f - z_c)$

Ellipse Focus $(x_f + x_c, z_f + z_c)$

TX Focus $(x_f, z_f)$

Beam Direction

Imaging Scanline a c b $d_{c1}$ $d_{c2}$ $$SNR(d) = 10 \times \log_{10} \left( \frac{P_{echo}(z)}{P_{noise}(z)} \right)$$

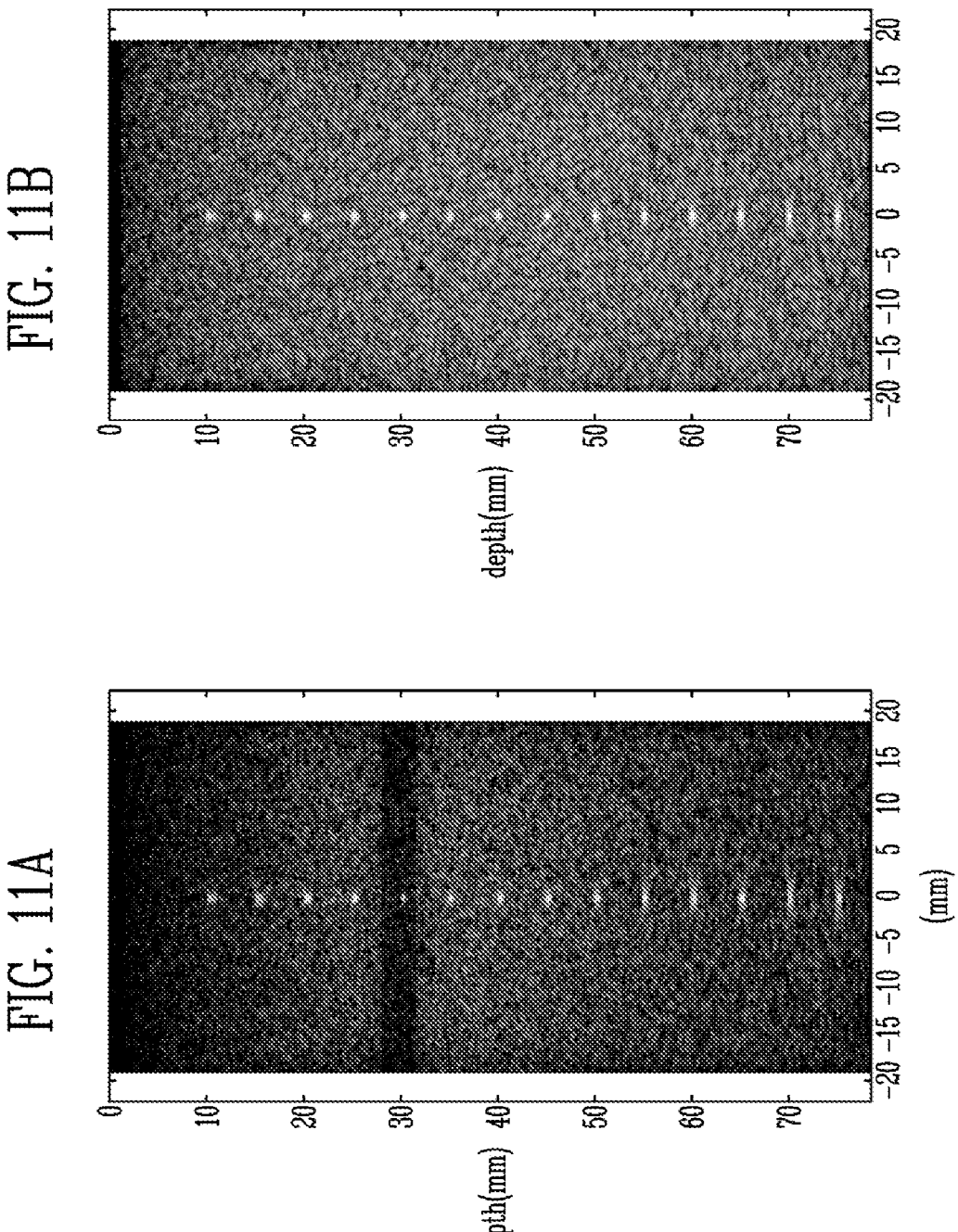

FIG. 14

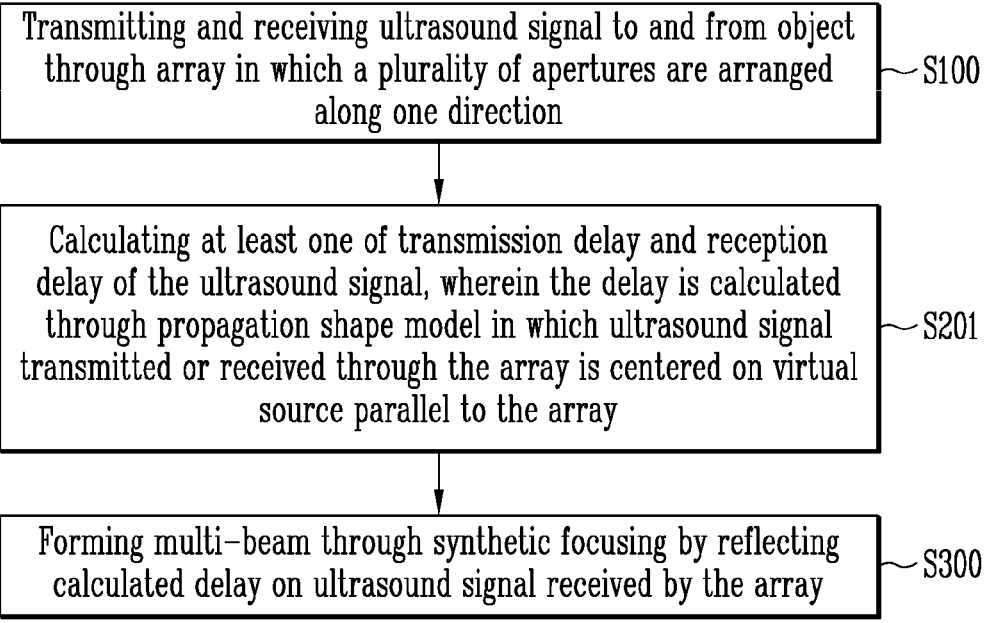

Transmitting and receiving ultrasound signal to and from object through array in which a plurality of apertures are arranged along one direction    ~S100

Calculating at least one of transmission delay and reception delay of the ultrasound signal, wherein the delay is calculated through propagation shape model in which ultrasound signal transmitted or received through the array is centered on virtual source parallel to the array    ~S201

Forming multi-beam through synthetic focusing by reflecting calculated delay on ultrasound signal received by the array    ~S300

1

ULTRASOUND IMAGE PROCESSING METHOD, AND ULTRASOUND APPARATUS USING THE SAME

CROSS-REFERENCE TO RELATED APPLICATION

The present application claims priority under 35 U.S.C. § 119(a) to Korean patent application number 10-2022-0062344 filed on May 20, 2022, and 10-2022-0154810 filed on Nov. 17, 2022 in the Korean Intellectual Property Office, the entire disclosure of which is incorporated by reference herein.

BACKGROUND

1. Technical Field

The present disclosure relates to an ultrasound image processing method and an ultrasound apparatus using the same, and more particularly, to an ultrasound image processing method for minimizing image distortion occurring at a focal depth of an ultrasound image, and an ultrasound apparatus using the same.

2. Related Art

Ultrasound diagnosis apparatuses have been used since the 1950s and are currently widely used as diagnostic imaging equipment in most hospitals through steady technological development. An ultrasound diagnosis apparatus is an apparatus that irradiates an ultrasound signal generated from a transducer of a probe to an object, receives information of an echo signal reflected from the object, and obtains an image of a part inside the object, and such an ultrasound diagnosis apparatus has advantages in that it has higher stability than a diagnosis apparatus using X-rays and can display an image in real time.

Resolution in an ultrasound image is divided into resolution in an axial direction and a resolution in a lateral direction. In general, the resolution in the axial direction is related to the width of the spectrum of an ultrasound beam. In order to increase the resolution in the axial direction, a pulse type signal with a small time width may be used. The resolution in the lateral direction is generally determined by the width of the main lobe, and it depends on the size of the probe and the frequency used, and because of diffraction, the beam spreads as the ultrasound travels through the object, making it lower than the resolution in the axial direction. As a method of increasing the resolution of the lateral direction in the ultrasound image, a focusing method is used. In focusing, there is a synthetic focusing method in which several sound fields obtained at different times are overlapped and synthesized.

The conventional synthetic aperture method is a technique using spherical waves, and has a disadvantage in that the resolution is greatly reduced at a long distance because the beam width increases as the observation depth increases due to the diffraction phenomenon of ultrasonic waves.

SUMMARY

Embodiments provide an ultrasound image processing method and an ultrasound apparatus using the same, which prevent image distortion by calculating a transmission delay using two-dimensional virtual sources in an ultrasound synthetic aperture focusing process.

In accordance with an aspect of the present disclosure, there is provided an ultrasound image processing method including transmitting and receiving an ultrasound signal to and from an object through an array in which a plurality of apertures are arranged along one direction, calculating at least one of a transmission delay and a reception delay of the ultrasound signal, and forming a multi-beam through synthetic focusing by reflecting the calculated delay on the ultrasound signal received by the array, wherein the calculating of at least one of the transmission delay and the reception delay includes calculating the delay through a propagation shape model in which the ultrasound signal transmitted or received through the array is centered on virtual sources parallel to the array.

Specifically, the virtual sources may be at least two-dimensional.

Specifically, the calculating of at least one of the transmission delay and the reception delay may include calculating the delay through a propagation shape model in which a line is formed by a part having a minimum width in a longitudinal direction of the array in a propagation shape of the ultrasound signal transmitted or received through the array.

Specifically, the virtual sources may be at least one of a line or an ellipse.

Specifically, the forming of the multi-beam may be performed for different locations, and may further include generating an image by synthesizing the multi-beams for different locations.

Specifically, waveforms emanating from the virtual sources may have an elliptical shape.

In accordance with another aspect of the present disclosure, there is provided an ultrasound image processing method including transmitting and receiving an ultrasound signal to and from an object through an array in which a plurality of apertures are arranged along one direction, calculating at least one of a transmission delay and a reception delay of the ultrasound signal, and forming a multi-beam through synthetic focusing by reflecting the calculated delay on the ultrasound signal received by the array, wherein the calculating of at least one of the transmission delay and the reception delay uses a virtual ellipse as virtual sources, and no discontinuous point of the transmission delay appears in a scan line formed between two focuses of the virtual ellipse.

Specifically, the forming of the multi-beam may be performed for different locations, and may further include generating an image by synthesizing the multi-beams for different locations.

Specifically, an interval of the scan line may be different for each image depth.

Specifically, lengths of a major axis and a minor axis of the virtual ellipse may be different for each image depth.

In accordance with another aspect of the present disclosure, there is provided an ultrasound apparatus including a transceiver configured to transmit and receive an ultrasound signal to and from an object through an array in which a plurality of apertures are arranged along one direction, a transceiving delay calculator configured to calculate at least one of a transmission delay and a reception delay of the ultrasound signal, and a multi-beam former configured to form a multi-beam through synthetic focusing by reflecting the calculated delay on the ultrasound signal received by the array, wherein the transceiving delay calculator is configured to calculate the delay through a propagation shape model in which the ultrasound signal transmitted or received through the array is centered on virtual sources parallel to the array.

Specifically, the virtual sources may be at least two-dimensional.

Specifically, the transceiving delay calculator may be configured to calculate the delay through a propagation shape model in which a line is formed by a part having a minimum width in a longitudinal direction of the array in a propagation shape of the ultrasound signal transmitted or received through the array.

Specifically, the virtual sources may be at least one of a line or an ellipse.

Specifically, the multi-beam former may be performed for different locations, and may be configured to generate an image by synthesizing the multi-beams for different locations.

Specifically, waveforms emanating from the virtual sources have an elliptical shape.

In accordance with another aspect of the present disclosure, there is provided an ultrasound apparatus, including a transceiver configured to transmit and receive an ultrasound signal to and from an object through an array in which a plurality of apertures are arranged along one direction, a transceiving delay calculator configured to calculate at least one of a transmission delay and a reception delay of the ultrasound signal, and a multi-beam former configured to form a multi-beam through synthetic focusing by reflecting the calculated delay on the ultrasound signal received by the array, wherein the transceiving delay calculator is configured to use a virtual ellipse as virtual sources, and no discontinuous point of the transmission delay appears in a scan line formed between two focuses of the virtual ellipse.

Specifically, the multi-beam former may be performed for different locations, and may generate an image by synthesizing the multi-beams for different locations.

Specifically, an interval of the scan line may be different for each image depth.

Specifically, lengths of a major axis and a minor axis of the virtual ellipse may be different for each image depth.

An ultrasound image processing method and an ultrasound apparatus using the same according to embodiments of the present disclosure can prevent image distortion occurring at a focal depth of an ultrasound image.

The effects of the present disclosure are not limited to the above-described effects, and effects not mentioned will be clearly understood by those skilled in the art from the present specification and the accompanying drawings.

BRIEF DESCRIPTION OF THE DRAWINGS

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey the scope of the example embodiments to those skilled in the art.

In the drawing figures, dimensions may be exaggerated for clarity of illustration. It will be understood that when an element is referred to as being "between" two elements, it can be the only element between the two elements, or one or more intervening elements may also be present. Like reference numerals refer to like elements throughout.

FIGS. 5A to 5C are perspective views of an ultrasound diagnosis apparatus 500 in accordance with at least one embodiment of the present disclosure.

FIGS. 6A to 6E are a diagram for explaining a conventional ultrasound synthetic aperture focusing method.

FIGS. 11A to 11B are a diagram for explaining a comparison between images according to each of a conventional method and an ultrasound synthetic aperture focusing method in accordance with the present disclosure.

FIG. 14 is a flowchart for explaining an image processing method according to an ultrasound apparatus 700 in accordance with an embodiment of the present disclosure.

DETAILED DESCRIPTION

Figure 1:
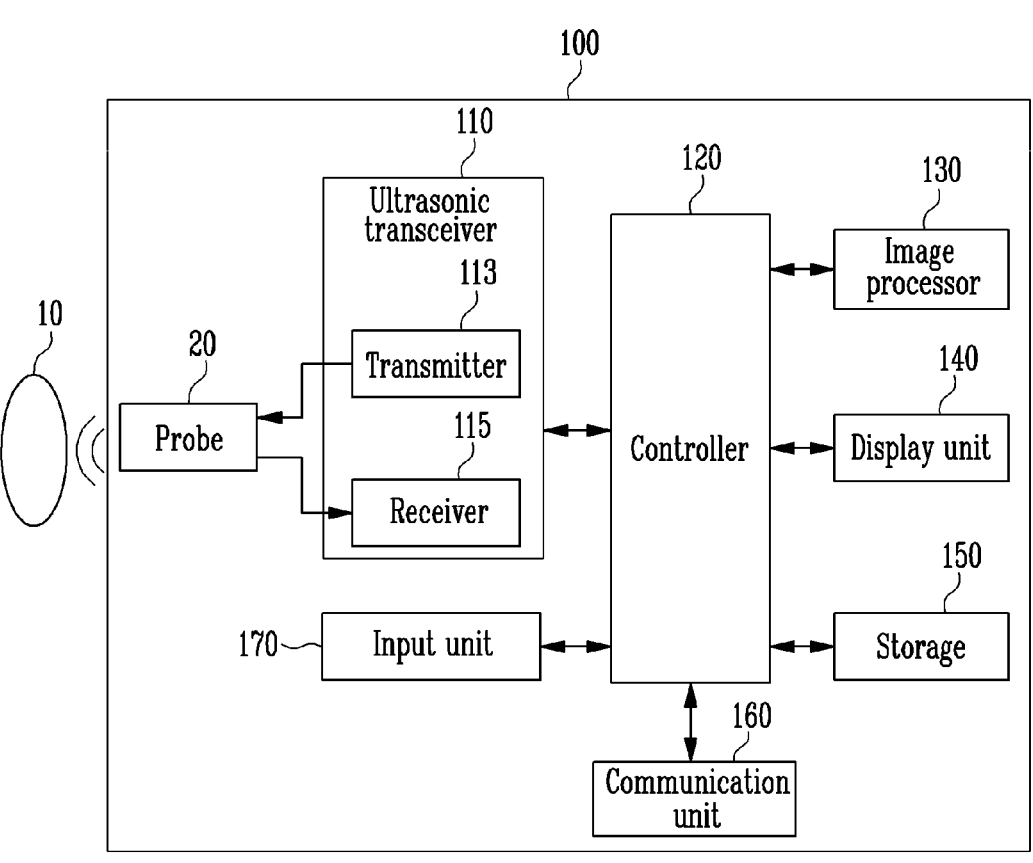
FIG. 1 is a block diagram illustrating a configuration of an ultrasound diagnosis apparatus 100 in accordance with any one embodiment of the present disclosure.

The present specification clarifies the scope of the present disclosure and, to enable those of ordinary skill in the art to which the present disclosure pertains to practice the present disclosure, the principle of the present disclosure is explained and embodiments are disclosed. The disclosed embodiments may be implemented in various forms.

Throughout the specification, when a part is "connected" to another part, it includes not only a case of being directly connected but also a case of being indirectly connected, and the indirect connection includes connection through a wireless communication network.

In addition, terms used herein are used to describe the embodiments, not intended to limit and/or restrict the disclosed invention. The singular expression includes the plural expression unless the context clearly dictates otherwise. In the present specification, terms such as "comprise" or "have" specify the presence of stated features, integers, steps, operations, elements, components or a combination thereof, but do not preclude the presence or addition of one or more other features, integers, steps, operations, elements, components, a combination thereof.

Further, although terms including ordinal numbers such as "first," "second," and the like are used to explain various components, the components are not limited to such terms and these terms are used only to distinguish one component from another component. For example, a first component may be referred to as a second component, or similarly, the second component may be referred to as the first component within the scope of the present disclosure.

In addition, terms such as "unit", "group", "block", "member", and "module" may refer to a unit that processes at least one function or operation. For example, the terms may refer to at least one process processed by at least one hardware such as a field-programmable gate array (FPGA)/application specific integrated circuit (ASIC), at least one software stored in a memory, or a processor.

Symbols given to each step are used to identify each step, and these signs do not indicate the order between the steps, and each step may be performed differently from the stated order unless the context clearly indicates a specific order.

In addition, an image herein may include a medical image acquired by a medical imaging apparatus such as a magnetic resonance imaging (MRI) apparatus, a computed tomography (CT) apparatus, an to ultrasound imaging apparatus, or an X-ray imaging apparatus, and ultrasound images and medical images of other modalities other than ultrasound may be provided or controlled.

Further, the term 'object' as used herein refers to a subject to be photographed, and may include human, animal, or a part thereof. For example, the object may include a part of the body (such as organs) or a phantom.

Throughout the specification, the term "ultrasound image" as used herein refers to an image for an object transmitted to the object and processed based on an ultrasound signal reflected from the object.

Hereinafter, an embodiment according to the present disclosure will be described in detail with reference to the accompanying drawings.

FIG. 1 is a block diagram illustrating a configuration of an ultrasound diagnosis apparatus 100 in accordance with any one embodiment of the present disclosure.

The ultrasound diagnosis apparatus 100 according to an embodiment of the present disclosure may include a probe 20, an ultrasonic transceiver 110, a controller 120, an image processor 130, a display unit 140, a storage 150, a communication unit 160, and an input unit 170.

The ultrasound diagnosis apparatus 100 may be provided not only as a cart type but also as a portable type. Examples of the portable ultrasound diagnosis apparatus may include a smart phone, a laptop computer, a PDA, and a tablet PC including a probe and an application, but are not limited thereto.

The probe 20 may include a plurality of transducers. The plurality of transducers may transmit an ultrasound signal to an object 10 according to a transmission signal applied from a transmitter 113. The plurality of transducers may be configured to receive the ultrasound signal reflected from the object 10 to generate a received signal. In addition, the probe 20 may be integrated with the ultrasound diagnosis apparatus 100 or may be provided as a separate type connected to the ultrasound diagnosis apparatus 100 by a wire or wirelessly. Moreover, the ultrasound diagnosis apparatus 100 may include one or a plurality of probes 20 according to an implementation form.

The controller 120 is configured to control, in consideration of the position and focal point of the plurality of transducers included in the probe 20, the transmitter 113 to generate a transmission signal to be applied to each of the plurality of transducers.

The controller 120 is configured to convert the received signal received from the probe 20 from analog to digital and, in consideration of the positions and focal points of the plurality of transducers, add the digitally converted received signals to control the receiver 115 to generate ultrasound data.

The image processor 130 is configured to generate an ultrasound image by using the ultrasound data generated by the ultrasound receiver 115.

Meanwhile, the ultrasound image may represent the motion of the object as a Doppler image as well as a gray scale ultrasound image obtained by scanning the object according to the A mode (amplitude mode), the B mode (brightness mode), and the M mode (motion mode).

A-mode is the most basic form of ultrasound image display method, which is a method that displays the intensity of the reflected sound as the amplitude size on the time (distance) axis, and if the reflected sound is strong, the amplitude is high, and if the reflected sound is weak, the amplitude is low, which is advantageous for distance measurement, but this mode is rarely used at present because the image changes even if the direction of the probe is slightly changed.

M-mode is a mode in which the distance of the moving reflector is displayed as a temporal change in the changed form of A-mode. By specifying the region of interest (ROI) in the 2D image as an M line and displaying the change over time in that area, it is mainly used to observe heart valves, and may also record fetal heart sounds, but has recently been replaced by the Doppler method.

B-mode is a method of displaying the reflected sound as the brightness of a dot, which is currently used in most ultrasound diagnostic equipment, and the brightness of each dot is proportional to the amplitude of the reflected signal, and recently provides a brightness level of 256 or more, and is also a mode in which long-term motions are visualized and displayed as they are in real time. The mode called 2D mode, which means B (brightness) mode, displays the cross-sectional image of an object in real time on the screen in black and white shades, and is the most used mode.

In addition, the Doppler mode is a mode that measures blood flow by detecting the flow of red blood cells in blood vessels in general, which uses the principle that the wavelength shortens when red blood cells approach the probe and lengthens when they move away, and there are color Doppler, pulse wave Doppler (PW), continuous wave Doppler (CW), etc., according to the method of displaying blood flow. The Doppler image may include a blood flow Doppler image showing blood flow (also called color Doppler image), a tissue Doppler image showing tissue movement and a spectral Doppler image displaying the moving speed of the object in a waveform.

In addition, as a composite mode, there are a mode in which two or three modes are simultaneously applied to one image to display other modes based on 2D, and a 3D mode in which a 3D stereoscopic image is displayed.

In the B-mode processing process, B-mode components are extracted and processed from ultrasound data, and in the image generation process, an ultrasound image in which signal intensity is expressed as brightness may be generated based on the B mode component extracted in the B mode processing process. In the Doppler processing process, Doppler components are extracted from ultrasound data, and in the image generation process, a Doppler image expressing the motion of the object in color or waveform may be generated based on the extracted Doppler component.

In the image generation process, a 2D ultrasound image or a 3D image of the object may be generated, and an elastic image obtained by imaging the degree of deformation of the object according to pressure may also be generated. Furthermore, various types of additional information may be expressed as text or graphics on the ultrasound image. Meanwhile, the generated ultrasound image may be stored in a memory.

In the process of measuring the object in the ultrasound image, a measurement tool for measuring the object may be determined, and one of a plurality of measurement tools may be selected based on a user input.

For example, a measurement tool selection menu for selecting one of the plurality of measurement tools may be provided, and the measurement tool selection menu may be displayed on one screen together with the ultrasound image. In addition, the measurement tool selection menu may be displayed on a separate screen different from the touch screen on which the ultrasound image is displayed.

In addition, one of the plurality of measurement tools may be determined based on a user input for selecting one of the plurality of measurement items to be measured. The measurement item may include, but is not limited to, length, width, or angle.

As a user input for selecting one of the measurement items is received, a predetermined measurement tool may be determined corresponding to the selected measurement item.

The display unit 140 may be configured to display the generated ultrasound image and various information processed in the ultrasound diagnosis apparatus 100. The ultrasound diagnosis apparatus 100 may include one or a plurality of display units 140 according to an implementation form. In addition, the display unit 140 may be provided as a touch screen in combination with a touch panel.

The controller 120 may control the overall operation of the ultrasound diagnosis apparatus 100 and a signal flow between internal components of the ultrasound diagnosis apparatus 100. The controller 120 may include a memory configured to store a program or data for performing a function of the ultrasound diagnosis apparatus 100, and a processor configured to process a program or data. In addition, the controller 120 may be configured to receive a control signal from the input unit 170 or an external device to control the operation of the ultrasound diagnosis apparatus 100.

The ultrasound diagnosis apparatus 100 may include the communication unit 160 and be connected with an external device (e.g., a server, a medical device, a portable device (smartphones, tablet PCs, wearable devices, etc.)) through the communication unit 160.

The communication unit 160 may include one or more components that enable communication with the external device, including, for example, at least one of short-range communication modules, wired communication modules, and wireless communication modules.

It is also possible that the communication unit 160 receives a control signal and data from the external device and transmits the received control signal to the controller 120 so as to have the controller 120 control the ultrasound diagnosis apparatus 100 according to the received control signal.

Alternatively, it is also possible that the controller 120 transmits a control signal to the external device through the communication unit 160 to control the external device in accordance with the control signal of the controller.

For example, the external device may be configured to process data of the external device in accordance with the control signal of the controller received through the communication unit.

A program (such as artificial intelligence) capable of controlling the ultrasound diagnosis apparatus 100 may be installed in the external device, such that the program may include instructions for performing some or all of the operations of the controller 120.

The program may be preinstalled in the external device or may be installed by downloading, by a user of the external device, the program from a server that provides an application. The server providing the application may include a recording medium in which the corresponding program is stored.

In addition, the program may include a storage medium of a server or a storage medium of a client device in a system consisting of a server and a client device. Alternatively, if there is a third device (smartphones, tablet PCs, wearable devices, etc.) that is communicatively connected to the server or client device, the program product may include a storage medium of the third device. Alternatively, the program may include a S/W program itself transmitted from the server to the client device or the third device, or transmitted from the third device to the client device.

In this case, one of the server, the client device, and the third device may execute the program to perform methods according to the disclosed embodiments. Alternatively, two or more of the server, the client device, and the third device may execute the program to perform the methods according to the disclosed embodiments by distributing the methods.

For example, a server (e.g., a cloud server or an artificial intelligence server, etc.) may execute a program stored in the server, so as to control the client device that is communicatively connected to the server to perform the method according to the disclosed embodiments.

The storage 150 may be configured to store various data or programs for driving and controlling the ultrasound diagnosis apparatus 100, input/output ultrasound data, and an acquired ultrasound image.

The input unit 170 may be configured to receive a user input for controlling the ultrasound diagnosis apparatus 100. For example, the user input may include an input for manipulating a button, a keypad, a mouse, a trackball, a jog switch, a knob, etc., an input for touching a touch pad or a touch screen, a voice input, a motion input, and an input of biometric information (e.g., iris recognition, fingerprint recognition, etc.), to but is not limited thereto.

Figure 2:
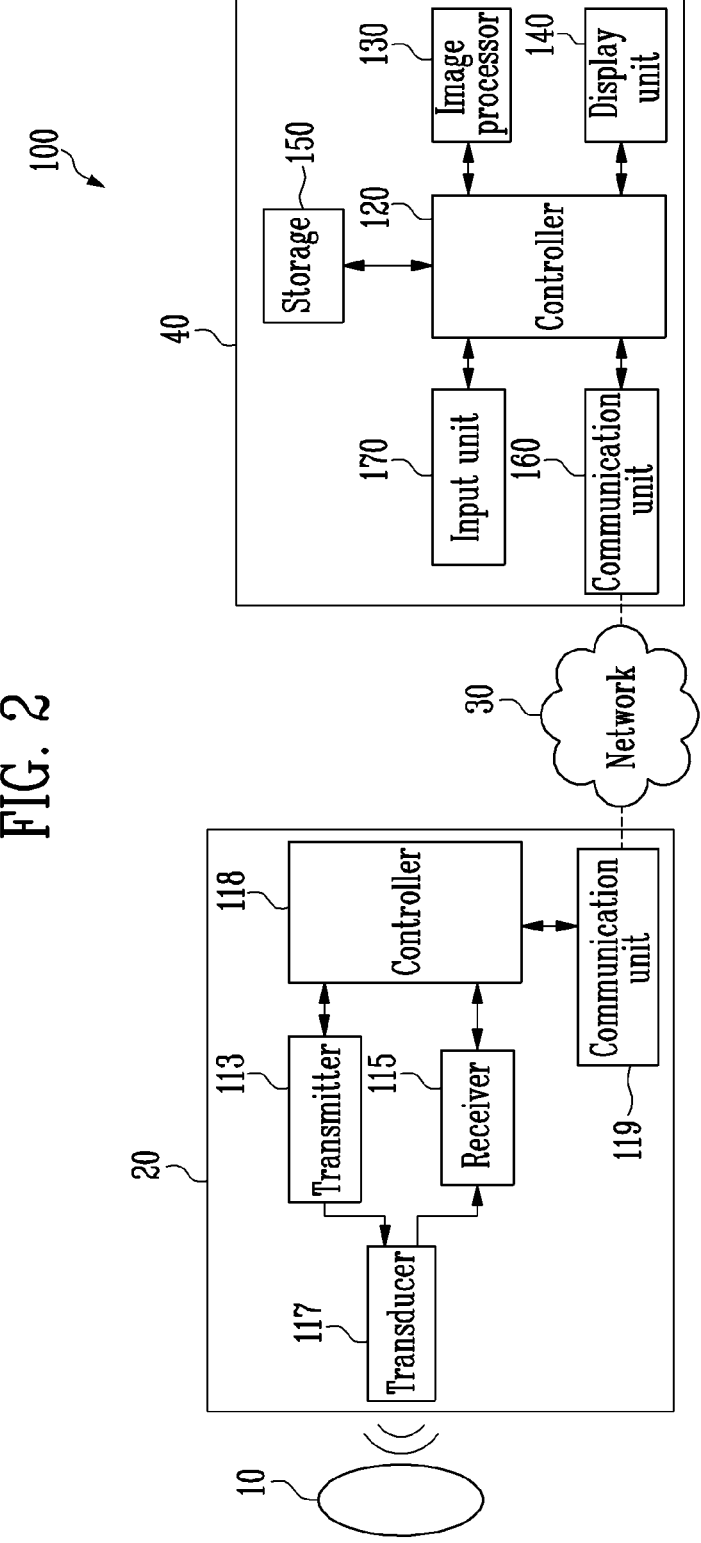
FIG. 2 is a block diagram illustrating a configuration of the ultrasound diagnosis apparatus 100 in accordance with any one embodiment of the present disclosure.

FIG. 2 is a block diagram illustrating a configuration of the ultrasound diagnosis apparatus 100 in accordance with any one embodiment of the present disclosure.

Referring to FIG. 2, the ultrasound diagnosis apparatus 100 may include a wireless probe 20 and an ultrasound system 40.

The wireless probe 20 may include the transmitter 113, a transducer 117, a receiver 115, a controller 118, and a communication unit 119. It is shown in FIG. 2 that the wireless probe 20 includes both the transmitter 113 and the receiver 115, but depending on the implementation, the wireless probe 20 may include only a part of the configuration of the transmitter 113 and the receiver 115, and a part of the configuration of the transmitter 113 and the receiver 115 may be included in the ultrasound system 40. Alternatively, the wireless probe 20 may further include the image processor 130.

The transducer 117 may include a plurality of transducers. The plurality of transducers may be configured to transmit an ultrasound signal to the object 10 according to a transmission signal transmitted from the transmitter 113. The plurality of transducers may be configured to receive the ultrasound signal reflected from the object 10 to generate a received signal.

The controller 118 is configured to control the transmitter 113 to generate a transmission signal to be transmitted to each of the plurality of transducers in consideration of the positions and focal points of the plurality of transducers.

The controller 118 is configured to convert the received signal received from the transducer 117 from analog to digital and, in consideration of the positions and focal points of the plurality of transducers, sum up the digitally converted received signals to control the receiver 155 to generate ultrasound data. Alternatively, when the wireless probe 20 includes the image processor 130, it is possible to generate an ultrasound image using the generated ultrasound data.

The communication unit 119 may be configured to wirelessly transmit the generated ultrasound data or ultrasound image to the ultrasound system 40 through a wireless network. Alternatively, the communication unit 119 may be configured to receive a control signal and data from the ultrasound system 40.

In addition, the ultrasound diagnosis apparatus 100 may include one or more wireless probes 20 according to an implementation form.

The ultrasound system 40 may be configured to receive ultrasound data or an ultrasound image from the wireless probe 20. The ultrasound system 40 may include the controller 120, the image processor 130, the display unit 140, the storage 150, the communication unit 160, and the input unit 170.

The image processor 130 may be configured to generate an ultrasound image by using the ultrasound data received from the wireless probe 20.

The display unit 140 may be configured to display an ultrasound image received from the wireless probe 20, an ultrasound image generated in the ultrasound system 40, and various information processed in the ultrasound diagnosis apparatus 100. The ultrasound diagnosis apparatus 100 may include one or a plurality of display units 140 according to an implementation form. In addition, the display unit 140 may be provided as a touch screen in combination with a touch panel.

The controller 120 may be configured to control the overall operation of the ultrasound diagnosis apparatus 100 and the signal flow among the internal components of the ultrasound diagnosis apparatus 100. The controller 120 may include a memory configured to store a program or data for performing a function of the ultrasound diagnosis apparatus 100, and a processor configured to process a program or data. Further, the controller 120 may be configured to receive a control signal from the input unit 170 or an external device to control the operation of the ultrasound diagnosis apparatus 100.

The ultrasound system 40 may include the communication unit 160 and be connected with the external device (e.g., a server, a medical device, a portable device (smartphones, tablet PCs, wearable devices, etc.)) through the communication unit 160.

The communication unit 160 may include one or more components that enable communication with the external device, including, for example, at least one of short-range communication modules, wired communication modules and wireless communication modules.

It is also possible that the communication unit 160 transmits and receives a control signal and data from the external device and transmits the received control signal to the controller 120 so as to have the controller 120 control the ultrasound diagnosis apparatus 100 according to the received control signal.

Alternatively, it is also possible that the controller 120 transmits a control signal to the external device through the communication unit 160 to control the external device in accordance with the control signal of the controller.

For example, the external device may be configured to process data of the external device in accordance with the control signal of the controller received through the communication unit.

A program (such as artificial intelligence) capable of controlling the ultrasound diagnosis apparatus 100 may be installed in the external device, such that the program may include instructions for performing some or all of the operations of the controller 120.

The program may be preinstalled in the external device or may be installed by downloading, by a user of the external device, the program from a server that provides an application. The server providing the application may include a recording medium in which the corresponding program is stored.

In addition, the program may include a storage medium of a server or a storage medium of a client device in a system consisting of a server and a client device. Alternatively, if there is a third device (smartphones, tablet PCs, wearable devices, etc.) that is communicatively connected to the server or client device, the program product may include a storage medium of the third device. Alternatively, the program may include a S/W program itself transmitted from the server to the client device or the third device, or transmitted from the third device to the client device.

In this case, one of the server, the client device, and the third device may execute the program to perform the methods according to the disclosed embodiments. Alternatively, the client device may perform the method according to the disclosed embodiments via the server.

Alternatively, two or more of the server, the client device, and the third device may execute the program for perform the methods according to the disclosed embodiments by distributing the methods.

For example, a server (e.g., a cloud server or an artificial intelligence server, etc.) may be configured to execute a program stored in the server, so as to control the client device that is communicatively connected to the server to perform the methods according to the disclosed embodiments.

The storage 150 may be configured to store various data or programs for driving and controlling the ultrasound diagnosis apparatus 100, input/output ultrasound data, and an ultrasound image.

The input unit 170 may be configured to receive a user input for controlling the ultrasound diagnosis apparatus 100. For example, the user input may include an input for manipulating a button, a keypad, a mouse, a trackball, a jog switch, a knob, etc., an input for touching a touch pad or a touch screen, a voice input, a motion input, and an input of biometric information (e.g., iris recognition, fingerprint recognition, etc.), but is not limited thereto.

Figure 3:
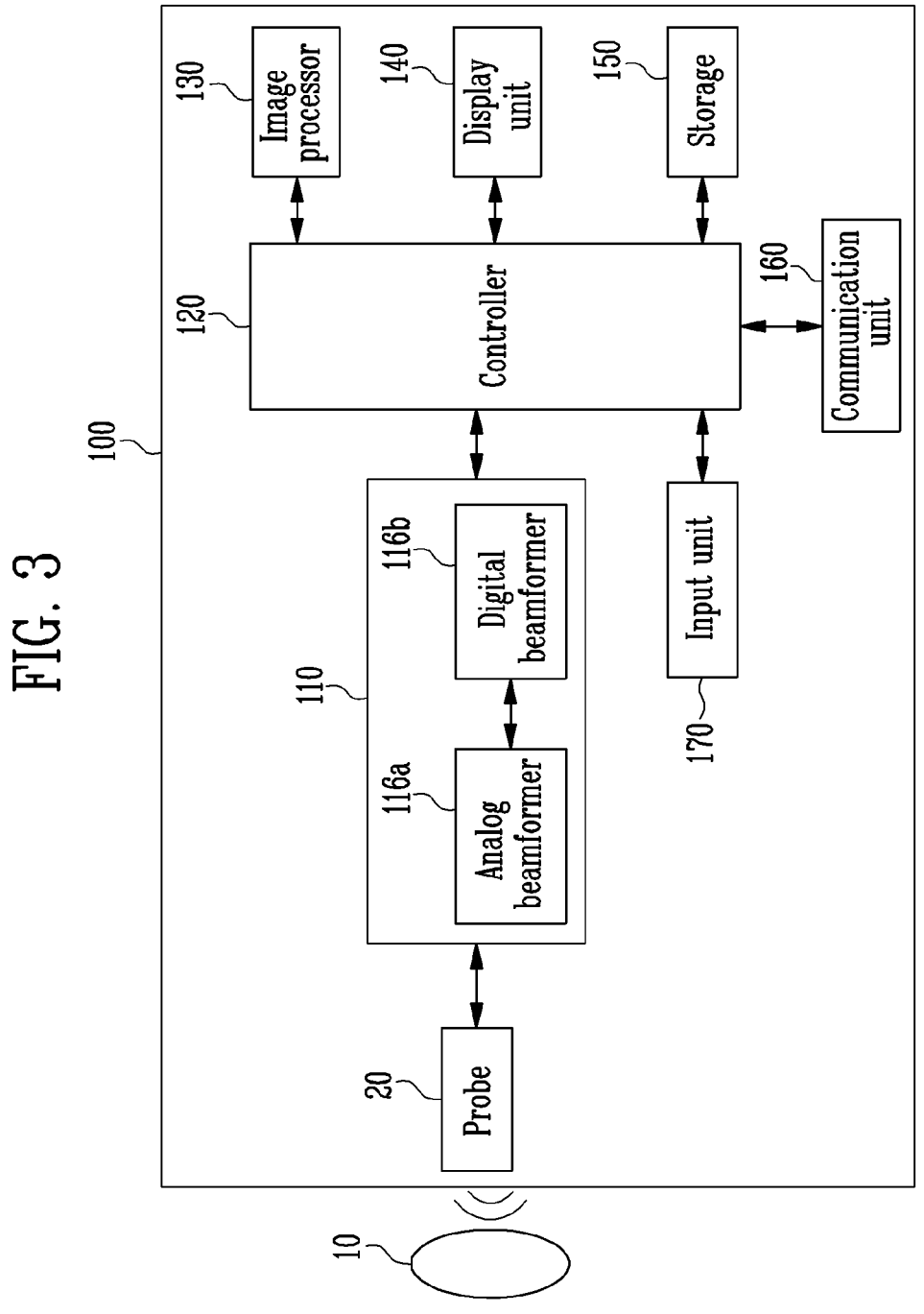
FIG. 3 is a block diagram illustrating a configuration of the ultrasound diagnosis apparatus 100 in accordance with any one embodiment of the present disclosure.

FIG. 3 is a block diagram illustrating a configuration of the ultrasound diagnosis apparatus 100 in accordance with any one embodiment of the present disclosure.

Referring to FIG. 3, the ultrasound diagnosis apparatus 100 may include a probe 20, an ultrasonic transceiver 110, a controller 120, an image processor 130, a display unit 140, an input unit 170, a storage 150, and a communication unit 160.

The probe 20 according to an embodiment of the present disclosure may include a plurality of transducers. The plurality of transducers may be arranged in two dimensions to form a 2D transducer array.

For example, the 2D transducer array may have a form including a plurality of sub-arrays including a plurality of transducers arranged in a first direction and in a second direction different from the first direction.

Further, the ultrasonic transceiver 110 may include an analog beamformer 116*a* and a digital beamformer 116*b*. Though the ultrasonic transceiver 110 and the probe 20 are illustrated as having a separate configuration in FIG. 3, the probe 20 according to an embodiment of the present disclosure may include partial or entire configuration of ultrasonic transceiver 110 according to the implementation form. For example, the probe 20 may include one or both of the analog beamformer 116*a* and the digital beamformer 116*b*.

The controller 120 may be configured to calculate a time delay value for digital beamforming for each sub-array with respect to each of the plurality of sub-arrays included in the 2D transducer array. Further, the controller 120 may be configured to calculate a time delay value for analog beamforming with respect to each of the transducers included in any one of the plurality of sub-arrays.

The controller 120 may be configured to control, according to the time delay value for analog beamforming and the time delay values for digital beamforming, the analog beamformer 116*a* and the digital beamformer 116*b* to generate a transmission signal to be transmitted to each of the plurality of transducers.

Further, the controller 120 may be configured to control the analog beamformer 116*a* to sum up the signals received from the plurality of transducers for each sub-array according to the time delay value for analog beamforming. In addition, the controller 120 may be configured to control the ultrasonic transceiver 110 to convert the signal summed for each sub-array from analog to digital. In addition, the controller 120 may be configured to control the digital beamformer 116*b* to generate ultrasound data by summing the digitally converted signals according to the time delay value for digital beamforming.

The image processor 130 is configured to generate an ultrasound image using the generated ultrasound data.

The display unit 140 may be configured to display the generated ultrasound image and various information processed in the ultrasound diagnosis apparatus 100. The ultrasound diagnosis apparatus 100 may include one or a plurality of display units 140 according to an implementation form. In addition, the display unit 140 may be provided as a touch screen in combination with a touch panel.

The controller 120 may be configured to control the overall operation of the ultrasound diagnosis apparatus 100 and the signal flow among the internal components in the ultrasound diagnosis apparatus 100. The controller 120 may include a memory configured to store a program or data for performing a function of the ultrasound diagnosis apparatus 100 and a processor configured to process a program or data. Further, the controller 120 may be configured to receive a control signal from the input unit 170 or the external device to control the operation of the ultrasound diagnosis apparatus 100.

The ultrasound diagnosis apparatus 100 may include the communication unit 160 and be connected with the external device (e.g., a server, a medical device, a portable device (smartphones, tablet PCs, wearable devices, etc.)) through the communication unit 160.

The communication unit 160 may include one or more components that enable communication with the external device, including, for example, at least one of short-range communication modules, wired communication modules and wireless communication modules.

It is possible that the communication unit 160 receives a control signal and data from the external device and transmits the received control signal to the controller 120 so as to have the controller 120 control the ultrasound diagnosis apparatus 100 according to the received control signal.

Alternatively, it is also possible that the controller 120 transmits the control signal to the external device through the communication unit 160 to control the external device according to the control signal of the controller.

For example, the external device may be configured to process data of the external device according to the control signal of the controller received through the communication unit.

A program (such as artificial intelligence) capable of controlling the ultrasound diagnosis apparatus 100 may be installed in the external device, such that the program may include instructions for performing some or all of the operations of the controller 120.

The program may be preinstalled in the external device or may be installed by downloading, by a user of the external device, the program from a server that provides an application. The server providing the application may include a recording medium in which the corresponding program is stored.

In addition, the program may include a storage medium of a server or a storage medium of a client device in a system consisting of a server and a client device. Alternatively, if there is a third device (smartphones, tablet PCs, wearable devices, etc.) that is communicatively connected to the server or client device, the program product may include a storage medium of the third device. Alternatively, the program may include a S/W program itself transmitted from the server to the client device or the third device, or transmitted from the third device to the client device.

In this case, one of the server, the client device, and the third device may execute the program to perform the methods according to the disclosed embodiments. Alternatively, two or more of the server, the client device, and the third device may execute the program to perform the methods according to the disclosed embodiments by distributing the methods.

For example, a server (e.g., a cloud server or an artificial intelligence server, etc.) may be configured to execute a program stored in the server, so as to control the client device that is communicatively connected to the server to perform the methods according to the disclosed embodiments.

The storage 150 may be configured to store various data or programs for driving and controlling the ultrasound diagnosis apparatus 100, input/output ultrasound data, and an ultrasound image.

The input unit 170 may be configured to receive a user input for controlling the ultrasound diagnosis apparatus 100. For example, the user input may include an input for manipulating a button, a keypad, a mouse, a trackball, a jog switch, a knob, etc., an input for touching a touch pad or a touch screen, a voice input, a motion input, and an input of biometric information (e.g., iris recognition, fingerprint recognition, etc.), but is not limited thereto.

Figures 4A, 4B, 4C:
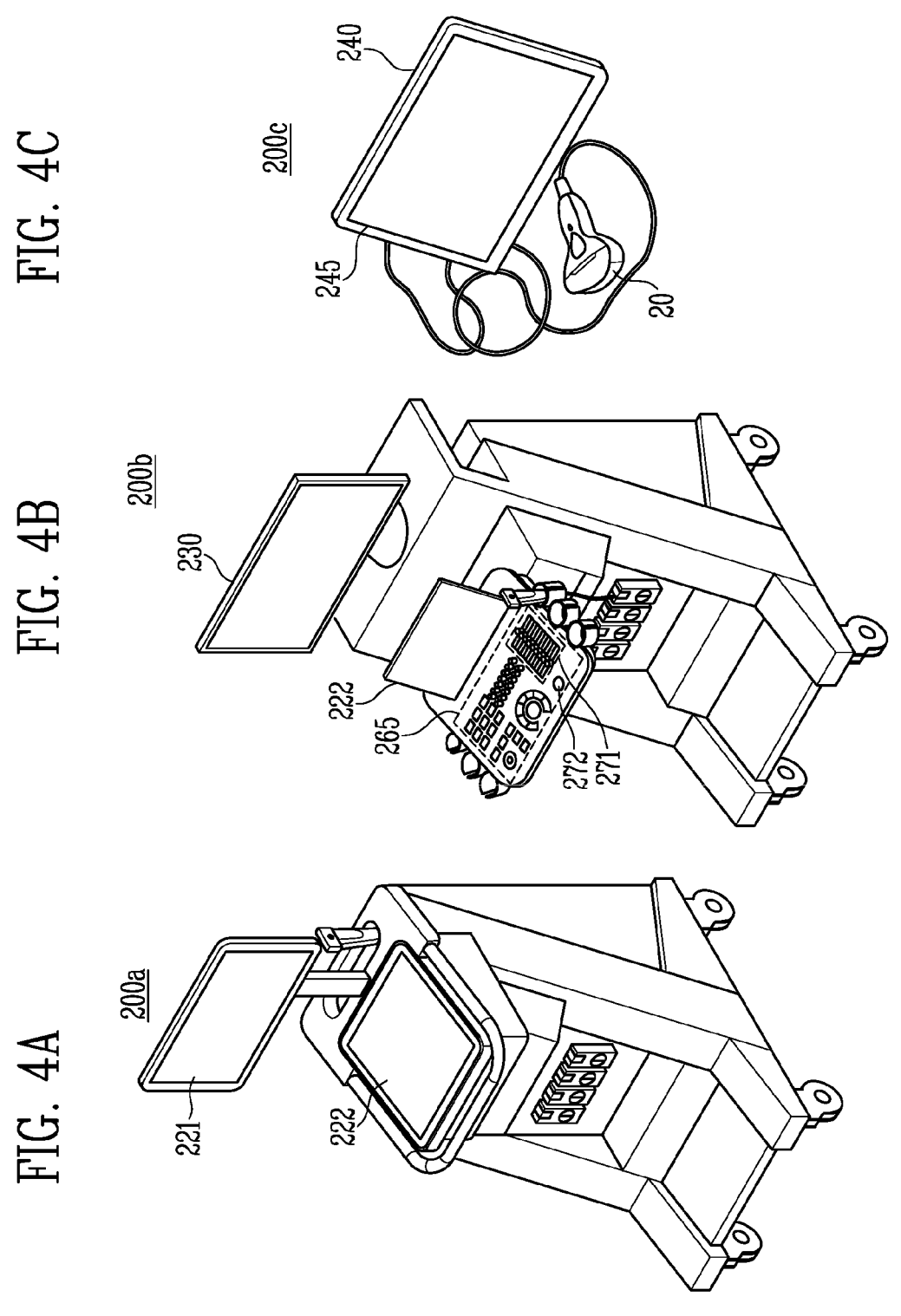
FIGS. 4A to 4C are perspective views of an ultrasound diagnosis apparatus 200 in accordance with at least one embodiment of the present disclosure.

FIGS. 4A to 4C are perspective views of an ultrasound diagnosis apparatus 200 in accordance with at least one embodiment of the present disclosure.

Referring to FIGS. 4A and 4B, the ultrasound diagnosis apparatuses 200a and 200b may include a main display unit 221 and a sub-display unit 222. One of the main display unit 221 and the sub-display unit 222 may be provided as a touch screen. The main display unit 221 and the sub-display unit 222 may be configured to display an ultrasound image or various information processed in the ultrasound diagnosis apparatuses 200a and 200b. In addition, the main display unit 221 and the sub-display unit 222 may be provided as a touch screen, and by providing a GUI, data for controlling the ultrasound diagnosis apparatuses 200a and 200b may be received from a user. For example, the main display unit 221 may be configured to display an ultrasound image, and the sub-display unit 222 may be configured to display a control panel for controlling the display of the ultrasound image in the form of a GUI. The sub-display unit 222 may be input with data for controlling the display of an image through a control panel displayed in the form of a GUI. The ultrasound diagnosis apparatuses 200a and 200b may be configured to control the display of the ultrasound image displayed on the main display unit 221 by using the received control data.

Referring to FIG. 4B, the ultrasound diagnosis apparatus 200b may further include a control panel 265 in addition to the main display unit 221 and the sub-display unit 222. The control panel 265 may include a button, a trackball, a jog switch, and a knob, and may be input with data for controlling the ultrasound diagnosis apparatus 200b from a user. For example, the control panel 265 may include a time gain compensation (TGC) button 271, and a freeze button 272. The TGC button 271 is a button for setting a TGC value for each depth of the ultrasound image. Further, when an input of the freeze button 272 is sensed while scanning the ultrasound image, the ultrasound diagnosis apparatus 200b may maintain a state in which a frame image at a corresponding moment is displayed.

Meanwhile, the button, the track ball, the jog switch and the knob included in the control panel 265 may be provided to the main display unit 221 or the sub-display unit 222 as a GUI.

Referring to FIG. 4C, the ultrasound diagnosis apparatus 200c may be implemented as a portable type. Examples of the portable ultrasound diagnosis apparatus 200c may include smart phones, laptop computers, PDAs, and tablet PCs including a probe and an application, but are not limited thereto.

The ultrasound diagnosis apparatus 200c may include the probe 20 and a main body 240, and the probe 20 may be connected to one side of the main body 240 by a wire or wirelessly. The main body 240 may include a touch screen 245. The touch screen 245 may be configured to display an ultrasound image, various information processed in the ultrasound diagnosis apparatus, and a GUI.

FIGS. 5A to 5C are perspective views of an ultrasound diagnosis apparatus 500 in accordance with at least one embodiment of the present disclosure.

Referring to FIG. 5A, the ultrasound diagnosis apparatus used indoors or an indoor ultrasound diagnosis apparatus 500 generally refers to a non-portable ultrasound diagnosis apparatus used for ultrasound diagnosis, and such an ultrasound diagnosis apparatus 500 is also called cart base equipment. Although the ultrasound diagnosis apparatus 500 is not necessarily used only indoors, it will be referred to as an indoor ultrasound diagnosis apparatus 500 for convenience.

The indoor ultrasound diagnosis apparatus 500 may have a portable docking unit 580 connected to a portable ultrasound diagnosis apparatus 400, and since all components except for the portable docking unit 580 of the indoor ultrasound diagnosis apparatus 500 used in an embodiment of the present disclosure are generally used, a detailed description thereof will be omitted.

Unlike the portable ultrasound diagnosis apparatus 400, the indoor ultrasound diagnosis apparatus 500 has fewer restrictions in terms of size, weight, power consumption, etc., so that diagnosable area is diverse, and it may be developed with high performance. When the portable ultrasound diagnosis apparatus 400 is mounted onto the indoor ultrasound diagnosis apparatus 500, it is possible to use the portable ultrasound diagnosis apparatus 400 with high performance. However, the position at which the portable ultrasound diagnosis apparatus 400 is mounted on the indoor ultrasound diagnosis apparatus 500 may be anywhere with no limitation where it is convenient for the user to use the portable ultrasound diagnosis apparatus 400 and the indoor ultrasound diagnosis apparatus 500 at the same time, and it is not limited by FIG. 5A. Furthermore, the portable ultrasound diagnosis apparatus 400 may be connected to the indoor ultrasound diagnosis apparatus 500 through a wire or integrally.

Referring to FIGS. 5A and 5B, the portable ultrasound diagnosis apparatus 400 in FIG. 5A may correspond to a portable ultrasound diagnosis apparatus 201 in FIG. 5B.

It may be integrated with a probe (not shown) including a plurality of transducer elements. Specifically, the portable ultrasound diagnosis apparatus 400 refers to an apparatus that is connected to the indoor ultrasound diagnosis apparatus 500 using a wireless or wired communication method (including Universal Serial Bus (USB)) to provide an ultrasound image to the user using received ultrasound image data. For example, the portable ultrasound diagnosis apparatus 400 may be a smart device in which an application is downloaded and installed in a smart phone.

Specifically, the portable ultrasound diagnosis apparatus 400 may be an apparatus that is connected to the indoor ultrasound diagnosis apparatus 500 through a wired or wireless communication method to provide an ultrasound image to the user using the received ultrasound image data.

For example, the wireless communication method may include at least one of short-range data communication methods including a 60 GHz (mmWave) wireless local area network (WLAN). It may be local area network (Wi-Fi), Bluetooth, ZigBee, Wi-Fi Direct (WFD), Infrared Data Association (IrDA), Bluetooth Low Energy (BLE), Near Field Communication (NFC), Wireless Broadband Internet (Wibro), globally interoperable Shared Wireless Access Protocol (SWAP) for Microwave Access (WiMAX), Wireless Gigabit Alliance (WiGig), and radio frequency (RF).

FIG. 5B illustrates an ultrasound diagnosis system in which the portable ultrasound diagnosis apparatus 201 is connected to a cart-based ultrasound diagnosis apparatus 500.

The cart-based ultrasound diagnosis apparatus 500 may be connected to the portable ultrasound diagnosis apparatus 201 using the aforementioned wireless communication method. Specifically, the portable ultrasound diagnosis apparatus 201 may include at least one wireless communication module (not shown) for performing at least one of the aforementioned wireless communication methods. Furthermore, a portable docking unit 580 in the cart-based ultrasound diagnosis apparatus 500 may include at least one wireless communication module (not shown) for performing wireless communication with the portable ultrasound diagnosis apparatus 201.

In this case, the wireless communication module in the cart-based ultrasound diagnosis apparatus 500 may be a module for performing communication according to at least one of the aforementioned wireless communication methods.

FIG. 5C illustrates an ultrasound diagnosis system in which the portable ultrasound diagnosis apparatus 202 is connected to the cart-based ultrasound diagnosis apparatus 500.

The portable ultrasound diagnosis apparatus 202 may be coupled to the probe 301 through a probe port. The portable ultrasound diagnosis apparatus 202 may be configured to generate an ultrasound image by using the ultrasound image corresponding to the ultrasound signal received by the probe 301 to display the ultrasound image on the display unit.

The cart-based ultrasound diagnosis apparatus 500 may be connected to the portable ultrasound diagnosis apparatus 202 using the aforementioned wireless communication method. The connection through wireless communication between the cart-based ultrasound diagnosis apparatus 500 and the portable ultrasound diagnosis apparatus 202 corresponds to the connection between the cart-based ultrasound diagnosis apparatus 500 and the portable ultrasound diagnosis apparatus 201, and thus a detailed description thereof will be omitted.

Hereinafter, an embodiment of an ultrasound apparatus that may be applied to at least any one of the ultrasound diagnostic apparatuses mentioned in FIGS. 1 to 3 mentioned above will be described.

FIGS. 6A to 6E are a diagram for explaining a conventional ultrasound synthetic aperture focusing method.

As shown in FIGS. 6, conventionally, channel data is obtained (FIG. 6A), transceiving delays are calculated, applied to signals, summed (FIG. 6B), and multiple scan lines for one transmission are formed as in FIG. 6C. Next, as in FIG. 6D, after applying a beam mask, synthetic aperture beam focusing was completed by overlapping scan lines for multiple transmissions (FIG. 6E).

As described above, the conventional method calculates the transceiving delay of an ultrasound beam by using a virtual source at the transmission beam focus, and a plurality of scan lines for one transmission was formed by applying the calculated transmission/reception delay to the acquired data.

Figures 7A, 7B, 7C:
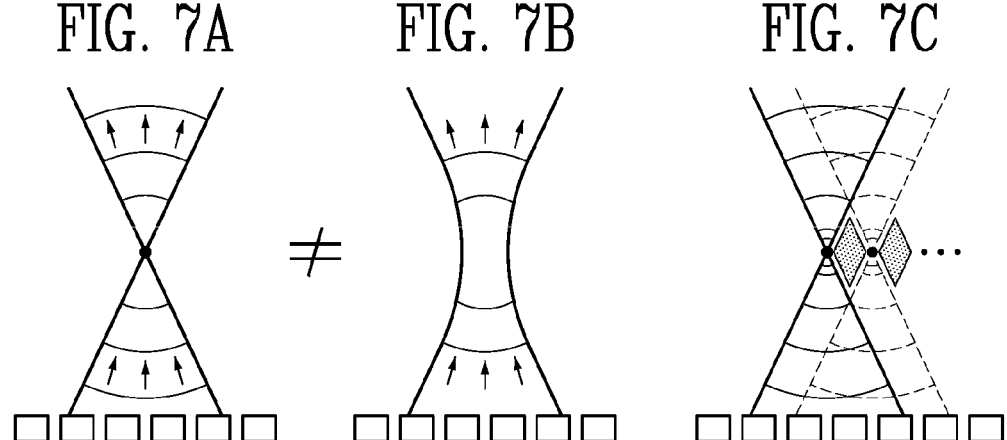
FIGS. 7A to 7C are is a diagram for explaining a conventional ultrasound synthetic aperture focusing method.

FIGS. 7A to 7C are a diagram for explaining a conventional ultrasound synthetic aperture focusing method.

As shown in FIGS. 7, the prior art calculates by assuming a circular transmission beam propagation shape centered on a virtual source.

FIG. 7A shows a conventional virtual source beam shape, and FIG. 7B shows an actual ultrasound beam propagation shape. When FIGS. 7A and 7B are compared, it may be confirmed that the transmission beam propagation shape centered on the virtual source is different from the actual ultrasound beam propagation shape.

As such, in the conventional method centered on a virtual source consisting of a single point, there is an inconsistency between the beam propagation shape calculated in the focal depth part of the ultrasound image and the actual beam propagation shape, and due to the inconsistency between these two shapes, as shown in FIG. 7C, a region that cannot overlap with the surrounding scan lines is created, and as a result, the gain and signal-to-noise ratio (SNR) of the ultrasound signal are reduced, resulting in a problem of the image being distorted.

An object of the present disclosure is to prevent an image distortion problem by improving a method of calculating a transceiving delay based on a conventional virtual source in a scanline synthesis process at a focal depth of an ultrasound image.

Figure 8A:
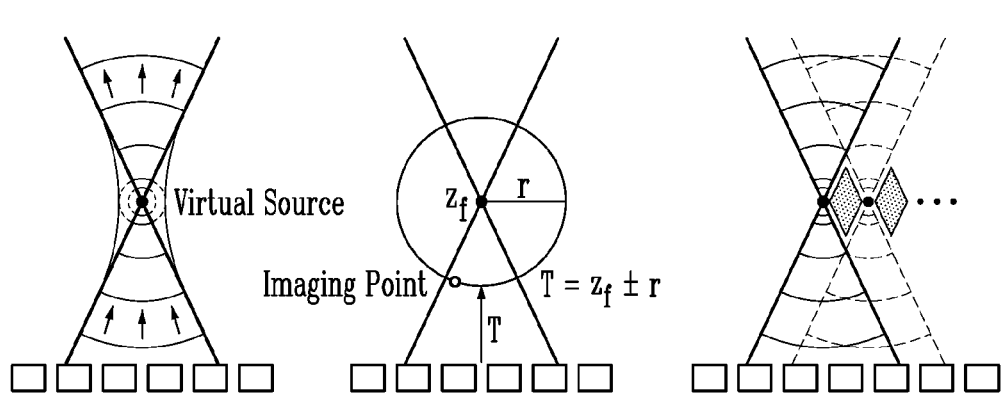
FIGS. 8A to 8B are a diagram for explaining a comparison between a conventional method and an ultrasound synthetic aperture focusing method in accordance with the present disclosure.
Figure 8B:
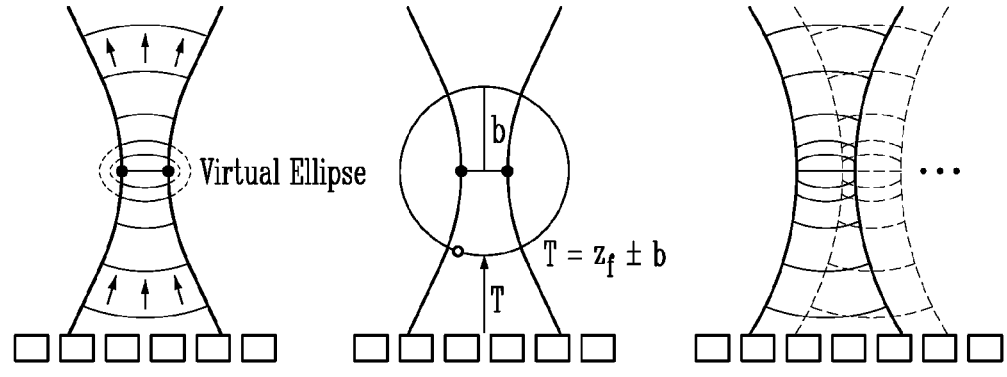

FIGS. 8A to 8B are a diagram for explaining a comparison between a conventional method and an ultrasound synthetic aperture focusing method in accordance with the present disclosure.

While FIG. 8A shows a process using a virtual source consisting of a single point in a conventional method, FIG. 8B shows a part of a process of calculating a transceiving delay of an ultrasound beam using a virtual ellipse rather than a conventional virtual source according to the method according to the present disclosure.

According to the present disclosure, a virtual ellipse in which two focuses are fixed has a flat shape around the beam focal depth, and when it is far from the beam focal depth, it becomes a shape approximate to a circle like a method using a conventional virtual image source, which can be confirmed through FIG. 8B.

As in the present disclosure, when using a virtual ellipse, it becomes a shape close to the actual ultrasound beam propagation shape, and as the scan line is synthesized at the focal depth in a shape similar to the actual ultrasound beam propagation shape, no discontinuous point of transmission delay appears in the scan line obtained between the two focuses. As a result, it is possible to prevent image distortion occurring in the focal depth part of the ultrasound image.

Figure 9A:
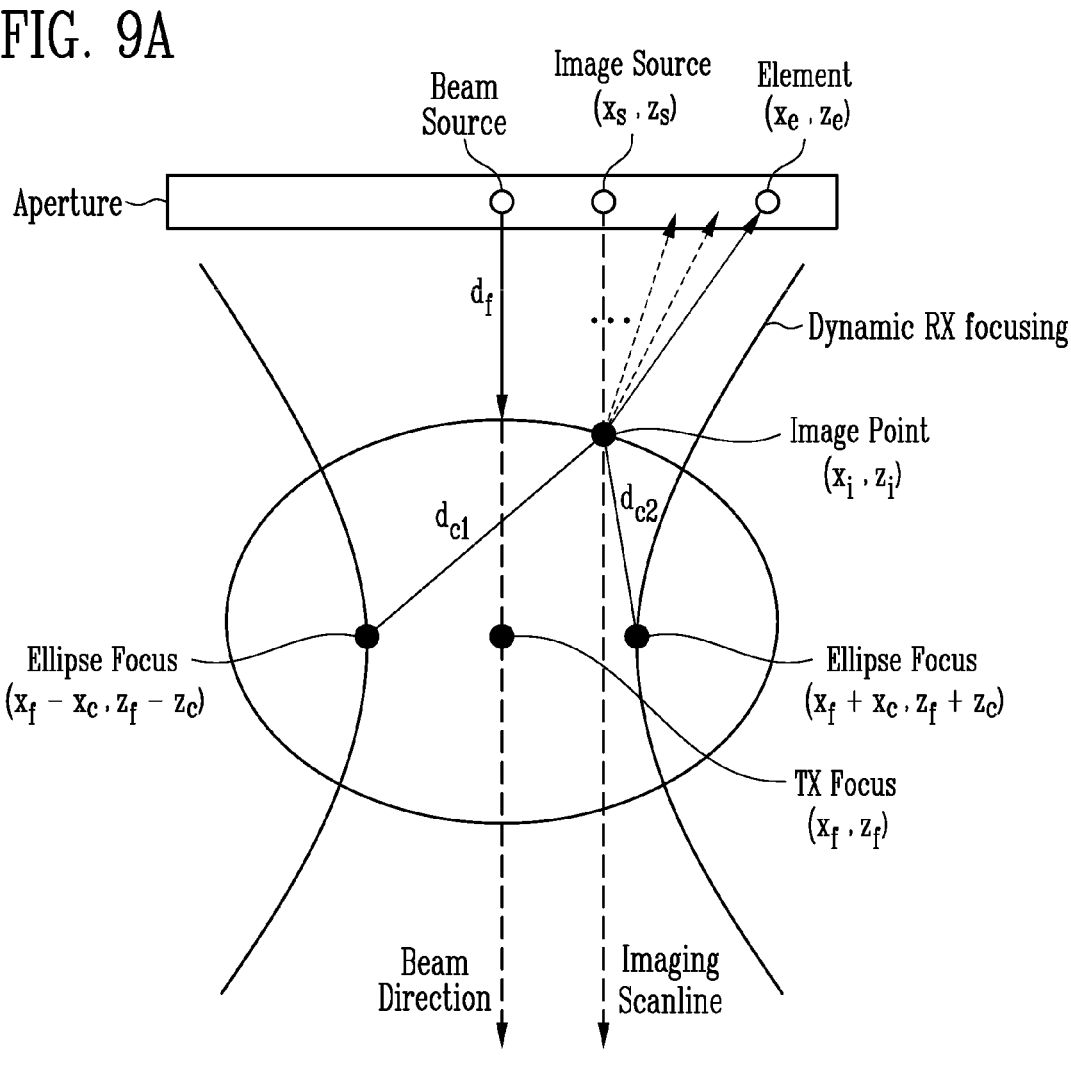
FIGS. 9A to 9B are a diagram for explaining an ultrasound synthetic aperture focusing method in accordance with the present disclosure.
Figure 9B:
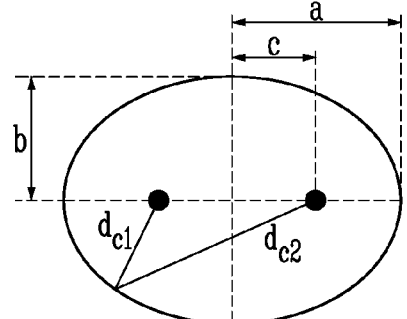

FIGS. 9A to 9B are a diagram for explaining an ultrasound synthetic aperture focusing method in accordance with the present disclosure.

FIG. 9 are a diagram illustrating a process of using a virtual ellipse in the ultrasound synthetic aperture focusing method according to the present disclosure, which is different in calculation method from conventionally using a virtual source consisting of one point.

As shown in FIG. 9A, on the aperture, the beam source, image source, and element are located, and when the TX focus is $(x_f, z_f)$, the ellipse focus can be represented by $(x_f-x_c, z_f-z_c)$ and $(x_f+x_c, z_f+z_c)$, respectively.

From FIG. 9B illustrating an ellipse, Equation (1) below can be used, and Equation (2) can be obtained by utilizing that delay is TX delay+RX delay, and as a result, Equation (3) can be calculated.

$$a^2 - c^2 = b^2 \tag{1}$$

$$2a = d_{c1} + d_{c2}$$

$$b = \sqrt{\left(\frac{d_{c1} + d_{c2}}{2}\right)^2 - c^2}$$

$$Tx\ \text{delay} = d_f \pm b \tag{2}$$

$$= d_f \pm \sqrt{\left(\frac{d_{c1} + d_{c2}}{2}\right)^2 - c^2}$$

$$d_f = \sqrt{(x_s - x_f)^2 + (z_s - z_f)^2} \tag{3}$$

$$d_{c1} = \sqrt{(x_f - x_c - x_i)^2 + (z_f - z_c - z_i)^2}$$

$$d_{c1} = \sqrt{(x_f + x_c - x_i)^2 + (z_f + z_c - z_i)^2}$$

Figure 10:
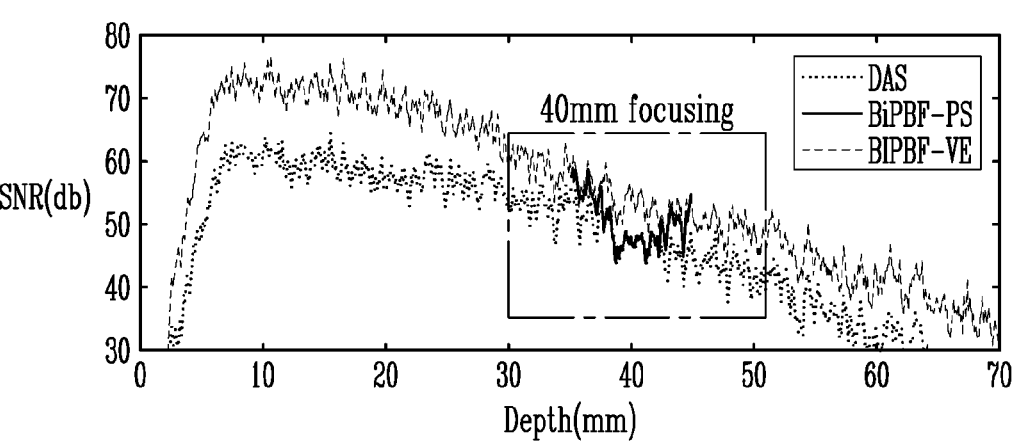
FIG. 10 is a diagram for explaining an ultrasound synthetic aperture focusing method in accordance with the present disclosure.

FIG. 10 is a diagram for explaining an ultrasound synthetic aperture focusing method in accordance with the present disclosure.

As can be seen in FIG. 10, the present disclosure may solve the problem of image distortion around the focal depth and improve the signal-to-noise ratio (SNR) around the focal depth by performing scan line synthesis so that no discontinuous point appears in the focal depth of the ultrasound image.

FIGS. 11A to 11B are a diagram for explaining a comparison between images according to each of a conventional method and an ultrasound synthetic aperture focusing method in accordance with the present disclosure.

FIG. 11A shows an image according to the conventional ultrasound synthetic aperture focusing method, and FIG. 11B shows an image according to the ultrasound synthetic aperture focusing method according to the present disclosure.

As can be seen through the comparison of FIGS. 11A and 11B, in the case of using the conventional ultrasound synthetic aperture focusing method, image distortion occurs around 30 mm, but in the case of using the ultrasound synthetic aperture focusing method according to the present disclosure, it can be confirmed that distortion does not occur in the vicinity.

Figure 12A:
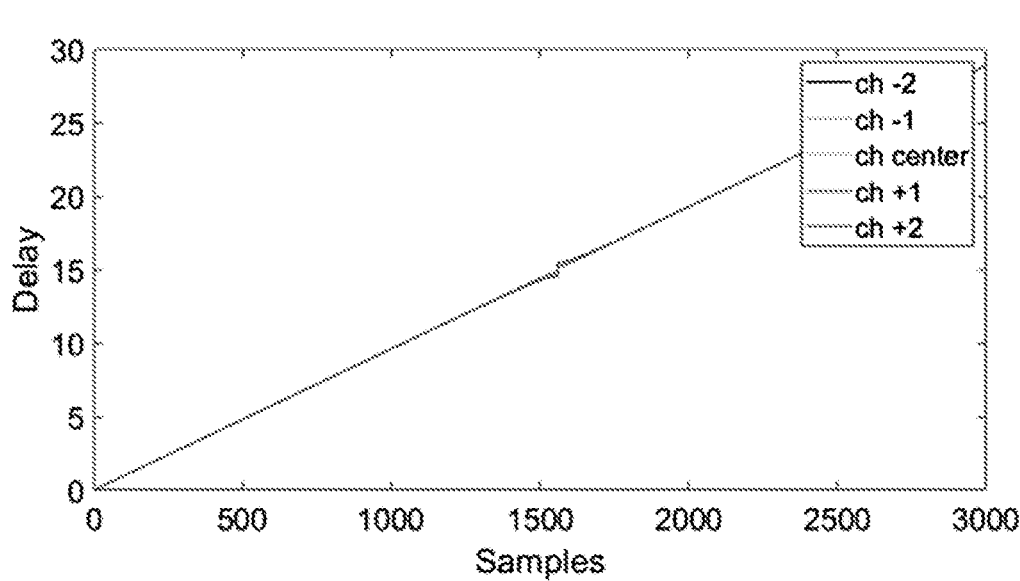
FIGS. 12A to 12B are a diagram for explaining a comparison between transmission delays according to each of a conventional method and an ultrasound synthetic aperture focusing method in accordance with the present disclosure.
Figure 12B:
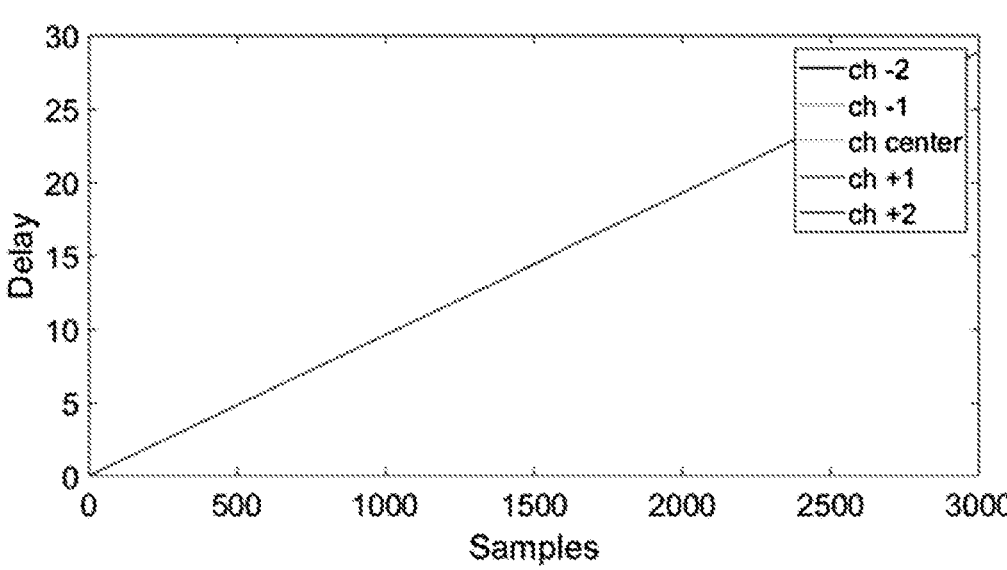

FIGS. 12A to 12B are a diagram for explaining a comparison between transmission delays according to each of a conventional method and an ultrasound synthetic aperture focusing method in accordance with the present disclosure.

FIG. 12A shows a transmission delay according to the conventional ultrasound synthetic aperture focusing method, and FIG. 12B shows a transmission delay according to the ultrasound synthetic aperture focusing method according to the present disclosure.

As can be seen through the comparison of FIG. 12A and FIG. 12B, it can be seen that the transmission delay in the synthetic aperture beam focusing using the virtual ellipse of the present disclosure is significantly reduced compared to the transmission delay in the conventional synthetic aperture beam focusing using the virtual source.

As described in FIGS. 8 to 12, the ultrasound synthetic aperture focusing method according to the present disclosure has significant effects compared to conventional methods.

Figure 13:
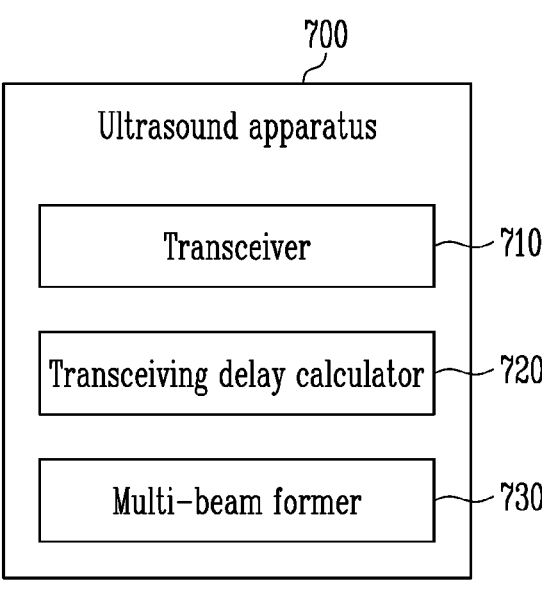
FIG. 13 is a diagram illustrating a configuration of an ultrasound apparatus 700 in accordance with an embodiment of the present disclosure.

FIG. 13 is a diagram illustrating a configuration of an ultrasound apparatus 700 in accordance with an embodiment of the present disclosure.

As shown in FIG. 13, an ultrasound apparatus 700 according to an embodiment of the present disclosure includes a transceiver 710 configured to transmit and receive an ultrasound signal to and from an object through an array in which a plurality of apertures are arranged along one direction, a transceiving delay calculator 720 configured to calculate at least one of a transmission delay and a reception delay of the ultrasound signal, and a multi-beam former 730 configured to form a multi-beam through synthetic focusing by reflecting the calculated delay on the ultrasound signal received by the array, wherein the transceiving delay calculator 720 is configured to calculate through a propagation shape model in which the ultrasound signal transmitted or received through the array is centered on virtual sources parallel to the array.

Unlike the conventional one consisting of a single point, the virtual sources in the present disclosure may be at least two-dimensional. Specifically, the ultrasound signal transmitted or received through the array may be two-dimensional virtual sources parallel to the array, but is not limited thereto and may be three-dimensional virtual sources if it has a thickness.

According to an embodiment, the transceiving delay calculator 720 in the present disclosure may calculate through the propagation shape model in which the part with the minimum width in the longitudinal direction of the array forms a line in the propagation shape of the ultrasound signal transmitted or received through the array.

The virtual sources in the present disclosure may be at least one of a line or an ellipse, and waveforms emanating from the virtual sources may have an elliptical shape.

In the present disclosure, by using a virtual ellipse, the scan line is synthesized at the focal depth in a shape similar to the actual ultrasound beam propagation shape by making the shape close to the actual ultrasound beam propagation shape.

In the scan line between the two focuses obtained in this way, there is a feature that no discontinuous point of transmission delay appears, and as a result, distortion of an image occurring in a focal depth part of an ultrasound image can be prevented.

The multi-beam former 730 of the present disclosure may be performed for different locations, and generate an image by synthesizing the multi-beams for different locations.

The ultrasound synthetic aperture focusing method according to the image processing method according to the ultrasound apparatus 700 of the present disclosure will be described with reference to FIG. 14 and below.

FIG. 14 is a flowchart for explaining an image processing method according to an ultrasound apparatus 700 in accordance with an embodiment of the present disclosure.

As shown in FIG. 14, an ultrasound image processing method by the ultrasound apparatus 700 according to an embodiment of the present disclosure includes transmitting and receiving an ultrasound signal to and from an object through an array in which a plurality of apertures are arranged along one direction S100, calculating at least one of a transmission delay and a reception delay of the ultrasound signal S201 and forming a multi-beam through synthetic focusing by reflecting the calculated delay on the ultrasound signal received by the array S300, wherein the calculating of the delay S201 is calculated through a propagation shape model in which the ultrasound signal transmitted or received through the array is centered on virtual sources parallel to the array.

According to an embodiment, the virtual sources are at least two-dimensional, and may be two-dimensional or three-dimensional as described above.

The calculating of the delay S201 according to the present disclosure may be calculated through the propagation shape model in which the part with the minimum width in the longitudinal direction of the array forms a line in the propagation shape of the ultrasound signal transmitted or received through the array.

Although not shown, forming of the multi-beam S300 may be performed for different locations, and further include generating an image by synthesizing the multi-beams for different locations.

Since details related to each step have been previously described in relation to the ultrasound apparatus 700 according to an embodiment of the present disclosure, a detailed description thereof will be omitted.

An ultrasound apparatus 700 according to another embodiment of the present disclosure includes a transceiver 710 configured to transmit and receive an ultrasound signal to and from an object through an array in which a plurality of apertures are arranged along one direction, a transceiving delay calculator 720 configured to calculate at least one of a transmission delay and a reception delay of the ultrasound signal, and a multi-beam former 730 configured to form a multi-beam through synthetic focusing by reflecting the calculated delay on the ultrasound signal received by the array. In particular, the transceiving delay calculator 720 according to another embodiment of the present disclosure uses a virtual ellipse as virtual sources, and is characterized in that no discontinuous point of transmission delay appears in a scan line formed between two focuses of a virtual ellipse.

Scan line intervals according to embodiments may be different for each image depth, and lengths of major and minor axes of a virtual ellipse may also be different for each image depth.

Figure 15:
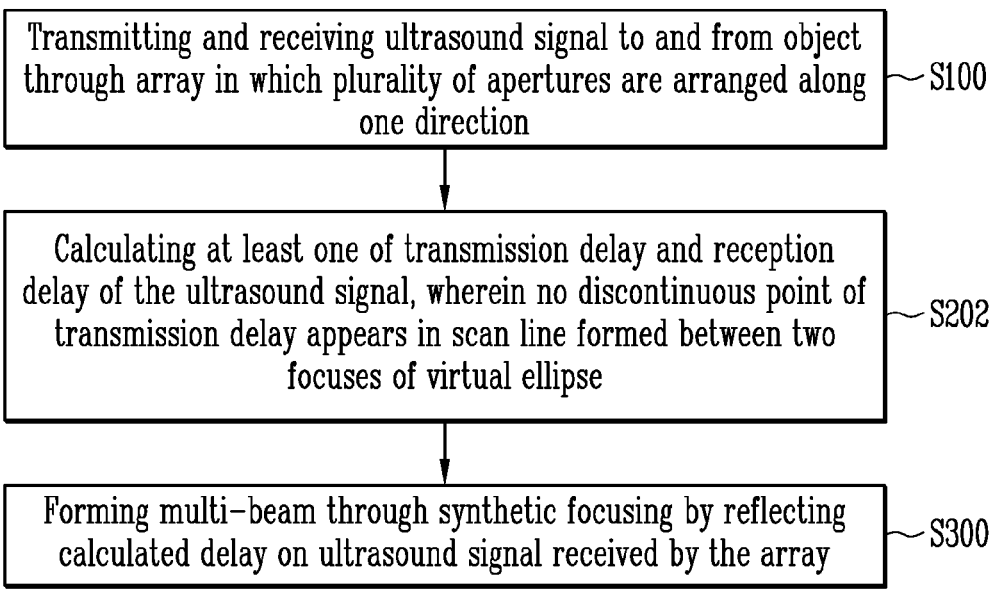
FIG. 15 is a flowchart for explaining an image processing method according to an ultrasound apparatus 700 in accordance with an embodiment of the present disclosure.

FIG. 15 is a flowchart for explaining an image processing method according to an ultrasound apparatus 700 in accordance with an embodiment of the present disclosure.

As shown in FIG. 15, an ultrasound image processing method by the ultrasound apparatus 700 according to another embodiment of the present disclosure includes transmitting and receiving an ultrasound signal to and from an object through an array in which a plurality of apertures are arranged along one direction S100, calculating at least one of a transmission delay and a reception delay of the ultrasound signal S202 and forming a multi-beam through synthetic focusing by reflecting the calculated delay on the ultrasound signal received by the array S300.

In particular, the calculating of the delay S202 according to another embodiment of the present disclosure uses a virtual ellipse as virtual sources, and is characterized in that no discontinuous point of transmission delay appears in a scan line formed between two focuses of a virtual ellipse.

The calculating of the transmission delay S202 according to embodiments may calculate the transmission delay time using the distance between the focuses, the focus depth, the distance to the image point, and the positional relationship between the probe elements, and the forming of the multi-beam S300 may be performed for different locations, and may further include generating an image by synthesizing the multi-beams for different locations.

The present disclosure uses a virtual ellipse rather than a conventionally used virtual source in the ultrasound synthetic aperture focusing process, and by calculating the transmission delay using a beam propagation shape similar to the actual ultrasound beam shape, which has a flat shape around the beam focal depth and has a shape approximate to a circle as it moves away, there is an effect of preventing image distortion through scan line synthesis at the focal depth.

Since details related to each step have been previously described in relation to the ultrasound apparatus 700 according to another embodiment of the present disclosure, a detailed description thereof will be omitted.

The disclosed embodiments have been described with reference to the accompanying drawings as described above. Those skilled in the art to which the present disclosure pertains will understand that the present disclosure may be practiced in forms different from the disclosed embodiments without changing the technical spirit or essential features of the present disclosure. The disclosed embodiments are illustrative and should not be construed as limiting.

What is claimed is:

1. An ultrasound image processing method, comprising:
transmitting and receiving an ultrasound signal to and from an object through an array in which a plurality of apertures is arranged along one direction;
obtaining at least one of a transmission delay and a reception delay of the ultrasound signal by calculating the delay using a propagation shape model in which the ultrasound signal transmitted or received through the array is centered on virtual sources parallel to the array, the virtual sources comprising a virtual ellipse having two fixed focus points with no discontinuous point of transmission delay appearing in a scan line formed between the two fixed focus points; and
forming a multi-beam at different locations through synthetic focusing by reflecting the calculated delay on the ultrasound signal received by the array,
wherein the transmission delay and the reception delay of the ultrasound signal are calculated as:

$$a^2 - c^2 = b^2 \qquad \text{equation (1)}$$

$$2a = d_{c1} + d_{c2}$$

$$b = \sqrt{\left(\frac{d_{c1} + d_{c2}}{2}\right)^2 - c^2}$$

$$Tx\ \text{delay} = d_f \pm b \qquad \text{equation (2)}$$

$$= d_f \pm \sqrt{\left(\frac{d_{c1} + d_{c2}}{2}\right)^2 - c^2},$$

in the equations (1) and the equation (2), a is a length of a major axis of the virtual ellipse, b is a length of a minor axis of the virtual ellipse, c is a distance along an X-axis direction from a center of the virtual ellipse to each of the two fixed focus points, and each of $d_{e1}$ and $d_{e2}$ is a distance from each of the two fixed focus points to image points $(x_i, z_i)$ on the virtual ellipse, and wherein $d_{e1}$, $d_{e2}$, and $d_f$ are derived as:

$$d_f = \sqrt{(x_s - x_f)^2 + (z_s - z_f)^2} \qquad \text{equation (3)}$$

$$d_{c1} = \sqrt{(x_f - x_c - x_i)^2 + (z_f - z_c - z_i)^2},$$

$$d_{c1} = \sqrt{(x_f + x_c - x_i)^2 + (z_f + z_c - z_i)^2}$$

in the equation (3), $d_f$ is a focal length.

2. The ultrasound image processing method of claim 1, wherein the virtual sources are at least two-dimensional.

3. The ultrasound image processing method of claim 1, wherein in the propagation shape model a line is formed by a part having a minimum width in a longitudinal direction of the array in a propagation shape of the ultrasound signal transmitted or received through the array.

4. The ultrasound image processing method of claim 1, wherein the forming of the multi-beam generating an image by synthesizing the multi-beams for different locations.

5. The ultrasound image processing method of claim 1, wherein waveforms emanate from the virtual sources.

6. An ultrasound image processing method, comprising:
transmitting and receiving an ultrasound signal to and from an object through an array in which a plurality of apertures is arranged along one direction;
obtaining at least one of a transmission delay and a reception delay of the ultrasound signal by using a distance between two fixed focus points of a virtual ellipse, focal depth, a distance to image point and a positional relationship between probe elements, wherein no discontinuous point of the transmission delay appears in a scan line formed between the two fixed focus points of the virtual ellipse; and forming a multi-beam at different locations through synthetic focusing by reflecting the calculated delay on the ultrasound signal received by the array, wherein the transmission delay and the reception delay of the ultrasound signal are calculated as:

$$a^2 - c^2 = b^2 \qquad \text{equation (1)}$$

$$2a = d_{c1} + d_{c2}$$

$$b = \sqrt{\left(\frac{d_{c1} + d_{c2}}{2}\right)^2 - c^2}$$

$$Tx \text{ delay} = d_f \pm b \qquad \text{equation (2)}$$

$$= d_f \pm \sqrt{\left(\frac{d_{c1} + d_{c2}}{2}\right)^2 - c^2},$$

in the equations (1) and the equation (2), a is a length of a major axis of the virtual ellipse, b is a length of a minor axis of the virtual ellipse, c is a distance along an X-axis direction from a center of the virtual ellipse to each of the two fixed focus points, and each of $d_{e1}$ and $d_{e2}$ is a distance from each of the two fixed focus points to image points $(x_i, z_i)$ on the virtual ellipse, and wherein $d_{e1}$, $d_{e2}$, and $d_f$ are derived as:

$$d_f = \sqrt{(x_s - x_f)^2 + (z_s - z_f)^2} \qquad \text{equation (3)}$$

$$d_{c1} = \sqrt{(x_f - x_c - x_i)^2 + (z_f - z_c - z_i)^2},$$

$$d_{c1} = \sqrt{(x_f + x_c - x_i)^2 + (z_f + z_c - z_i)^2}$$

in the equation (3), $d_f$ is a focal length.

7. The ultrasound image processing method of claim 6, wherein the forming of the multi-beam further comprises generating an image by synthesizing the multi-beams for different locations.

8. The ultrasound image processing method of claim 7, wherein an interval of the scan line is different for a depth of the image.

9. The ultrasound image processing method of claim 7, wherein lengths of a major axis and a minor axis of the virtual ellipse are different for a depth of the image.

10. An ultrasound apparatus, comprising:

a transceiver configured to transmit and receive an ultrasound signal to and from an object through an array in which a plurality of apertures is arranged along one direction;

a transceiving delay calculator configured to obtain at least one of a transmission delay and a reception delay of the ultrasound signal by calculating the delay using a propagation shape model in which the ultrasound signal transmitted or received through the array is centered on virtual sources parallel to the array, the virtual sources comprising a virtual ellipse having two fixed focus points with no discontinuous point of transmission delay appearing in a scan line formed between the two fixed focus points; and a multi-beam former configured to form a multi-beam at different locations through synthetic focusing by reflecting the calculated delay on the ultrasound signal received by the array, wherein the transmission delay and the reception delay of the ultrasound signal are calculated as:

$$a^2 - c^2 = b^2 \qquad \text{equation (1)}$$

$$2a = d_{c1} + d_{c2}$$

$$b = \sqrt{\left(\frac{d_{c1} + d_{c2}}{2}\right)^2 - c^2}$$

$$Tx \text{ delay} = d_f \pm b \qquad \text{equation (2)}$$

$$= d_f \pm \sqrt{\left(\frac{d_{c1} + d_{c2}}{2}\right)^2 - c^2},$$

in the equations (1) and the equation (2), a is a length of a major axis of the virtual ellipse, b is a length of a minor axis of the virtual ellipse, c is a distance along an X-axis direction from a center of the virtual ellipse to each of the two fixed focus points, and each of $d_{e1}$ and $d_{e2}$ is a distance from each of the two fixed focus points to image points $(x_i, z_i)$ on the virtual ellipse, and wherein $d_{e1}$, $d_{e2}$, and $d_f$ are derived as:

$$d_f = \sqrt{(x_s - x_f)^2 + (z_s - z_f)^2} \qquad \text{equation (3)}$$

$$d_{c1} = \sqrt{(x_f - x_c - x_i)^2 + (z_f - z_c - z_i)^2},$$

$$d_{c1} = \sqrt{(x_f + x_c - x_i)^2 + (z_f + z_c - z_i)^2}$$

in the equation (3), $d_f$ is a focal length.

11. The ultrasound apparatus of claim 10, wherein the virtual sources are at least two-dimensional.

12. The ultrasound apparatus of claim 10, wherein in the propagation shape model a line is formed by a part having a minimum width in a longitudinal direction of the array in a propagation shape of the ultrasound signal transmitted or received through the array.

13. The ultrasound apparatus of claim 10, wherein waveforms emanate from the virtual sources.

* * * * *